(12) United States Patent
Boudeman et al.

(10) Patent No.: US 11,023,037 B2
(45) Date of Patent: Jun. 1, 2021

(54) ADVANCED COMMUNICATION METHOD AND APPARATUS

(71) Applicants: Joseph J. Boudeman, Pacifica, CA (US); Joseph W. Boudeman, Pacifica, CA (US)

(72) Inventors: Joseph J. Boudeman, Pacifica, CA (US); Joseph W. Boudeman, Pacifica, CA (US)

( * ) Notice: Subject to any disclaimer, the term of this patent is extended or adjusted under 35 U.S.C. 154(b) by 0 days.

(21) Appl. No.: 16/746,705

(22) Filed: Jan. 17, 2020

(65) Prior Publication Data

US 2020/0233486 A1 Jul. 23, 2020

Related U.S. Application Data

(60) Provisional application No. 62/793,808, filed on Jan. 17, 2019.

(51) Int. Cl.
*G09G 5/00* (2006.01)
*G06F 3/01* (2006.01)

(52) U.S. Cl.
CPC .................................. *G06F 3/011* (2013.01)

(58) Field of Classification Search
CPC . G06F 3/01; G06F 3/011; G06F 3/012; G06F 3/013; G06F 3/015; G06F 3/016; A61M 1/00; H04M 1/00
See application file for complete search history.

(56) References Cited

U.S. PATENT DOCUMENTS

| 5,759,044 | A | * | 6/1998 | Redmond | G06F 3/012 348/383 |
| 6,347,261 | B1 | * | 2/2002 | Sakaue | B25J 9/1694 345/156 |
| 8,238,876 | B2 | * | 8/2012 | Teng | H04M 1/67 455/411 |
| 2007/0250119 | A1 | * | 10/2007 | Tyler | A61N 1/36103 607/2 |
| 2010/0114974 | A1 | * | 5/2010 | Jung | G06F 3/0414 707/802 |
| 2011/0210931 | A1 | * | 9/2011 | Shai | G10L 21/06 345/173 |
| 2014/0274010 | A1 | * | 9/2014 | Cavallaro | H04W 76/14 455/418 |
| 2016/0026253 | A1 | * | 1/2016 | Bradski | H04N 13/344 345/8 |
| 2017/0102172 | A1 | * | 4/2017 | Fu | G04B 47/068 |
| 2017/0160802 | A1 | * | 6/2017 | Hardee | H04N 21/47214 |
| 2017/0357324 | A1 | * | 12/2017 | Chaudhri | G06T 11/20 |
| 2019/0024350 | A1 | * | 1/2019 | Silverstein | E03C 1/0408 |
| 2019/0073077 | A1 | * | 3/2019 | Kim | G06F 3/044 |
| 2019/0339784 | A1 | * | 11/2019 | Lemay | G06F 3/0488 |

* cited by examiner

*Primary Examiner* — Joe H Cheng
(74) *Attorney, Agent, or Firm* — West & Associates, A PC; Stuart J. West; Charlotte Rodeen-Dickert

(57) ABSTRACT

An advanced system and method of communication wherein users can communicate via audio, visual, or haptic signals over a wireless network. Non-verbal communication can be conducted via a lip-reading system with video sensors and an interpretive software model, facial and eye movements, and other methods. In some embodiments, the apparatus can be contained within a helmet and/or other wearable device.

15 Claims, 13 Drawing Sheets

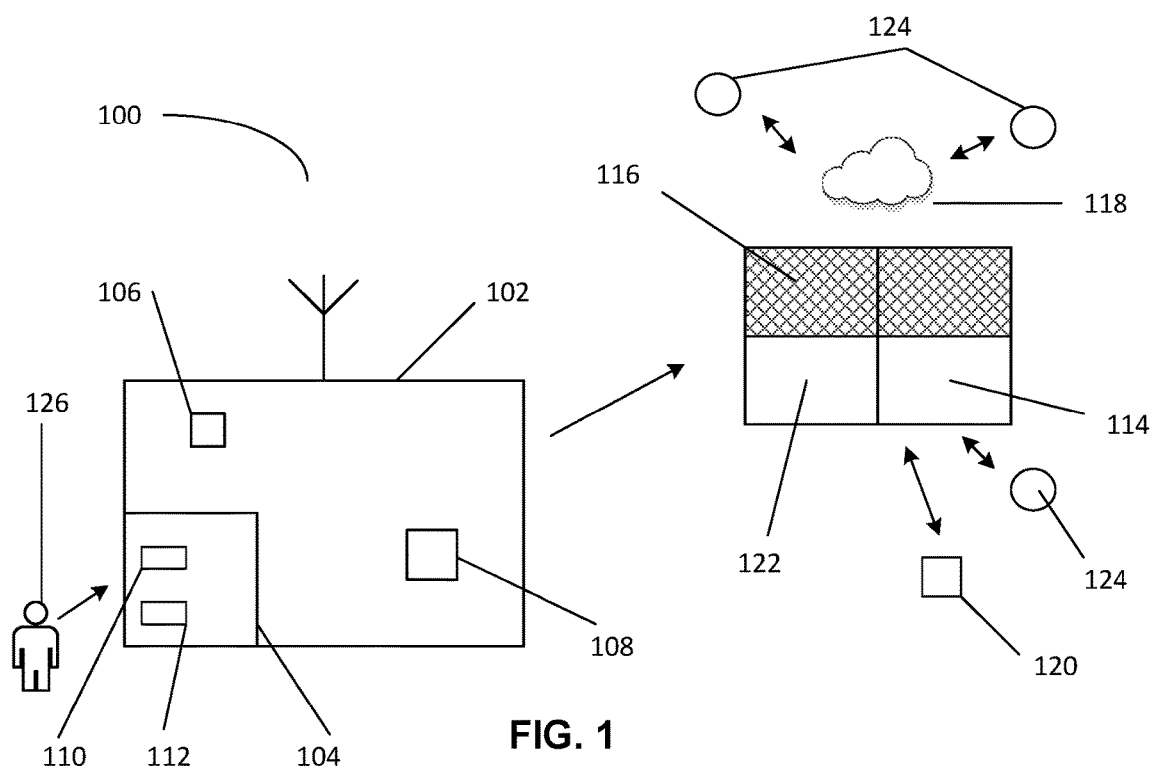
FIG. 1
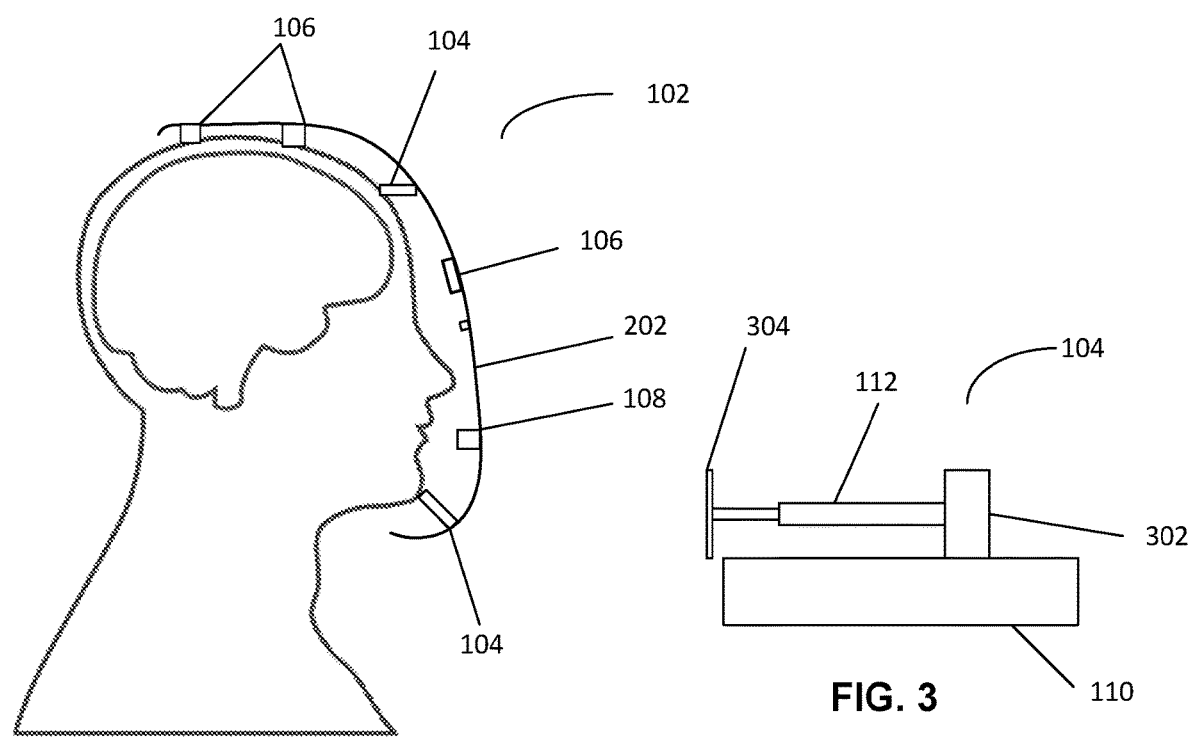
FIG. 2
FIG. 3

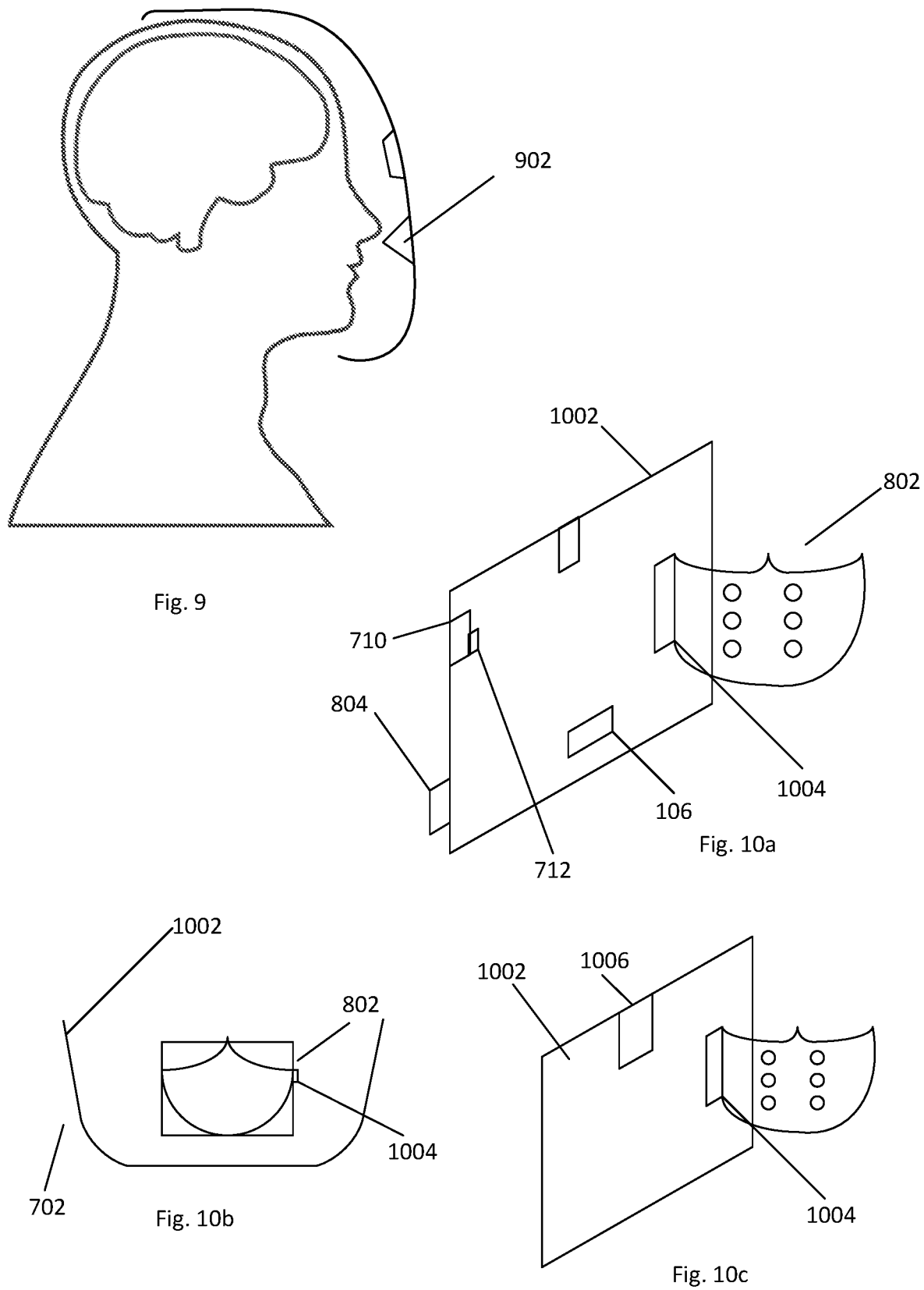

| condition/situation/event | input sensor/device | processor | output component | result |
|---|---|---|---|---|
| Lip motion in speech | video | Remote 114 | Audio 716/visual 602 units (other) Computer 122 | Comm Data coll |
| Facial movement | Video force/motion sensor | Remote 114 | Audio 716/visual 602 units (other) Computer 122 | Comm Data coll |
| Brain activity | EEG Temp/humid sensor (fNIRS) | Remote 114 | Audio 716/visual 602 units TDCS 1502 (other) Computer 122 | Comm Data coll |
| Auditory signals | Microphone | Remote 114 Internal 714 | Audio unit 716 (other) | Comm data coll |
| Visual signals | Video | Remote 114 Internal 714 | Computer 122 Visual unit 602 | Comm Data coll |
| Environmental | Temp/humid sensor | Remote 114 Internal 714 | Environmental control unit 710 | Data coll adj |
| Fit of UI 102 | Force, pressure sensor | Internal 714 | Adjustment units 104 Piezoelectrics | adj |

Fig. 15a

ADVANCED COMMUNICATION METHOD AND APPARATUS

CROSS-REFERENCE TO RELATED APPLICATION(S)

Claim of Priority

This application claims the benefit of priority of U.S. Provisional Application 62/793,808, filed Jan. 17, 2019, the complete contents of which is incorporated by reference herein.

BACKGROUND

Technical Field

The present device relates to the field of communication devices and more specifically to the field of verbal and non-verbal communication devices.

Background

The communication process between organisms and/or machine interactions is often complicated, time consuming and can result in waste and unintended results. In some cases, insufficient information is conveyed and/or in other cases information is conveyed ineffectively, resulting in poor comprehension or misunderstanding of the message.

Multiple communication devices exist that can facilitate communication, but these devices include inherent flaws. In some instances, they are incapable of accurately receiving and conveying messages due to unreliable sensing resulting from unreliable positioning and/or sensing of sensors and/or message delivery apparatuses.

What is needed is a communication device that can accurately sense vocal sounds, facial expressions, speech-related expressions, environmental conditions, and mental processes, and relay this information to a single or multiple entities.

BRIEF DESCRIPTION OF THE DRAWINGS

Further details of the present device are explained with the help of the attached drawings in which:

FIG. 1 depicts an overview diagram of an embodiment of the present system and method of advanced communication.

FIG. 2 depicts a side view diagram of an embodiment of a user interface of the present system and method.

FIG. 3 depicts a side view of an embodiment of an adjustment assembly of a user interface device in the present system and method.

FIG. 9 depicts an alternate embodiment of a user interface device for use in the system and method.

FIGS. 10*a*-10*c* depict various views of a component of a user interface device for use in the system and method.

FIG. 15*a* depicts a functional overview of an embodiment of the present system and method.

DETAILED DESCRIPTION

Figure 4:
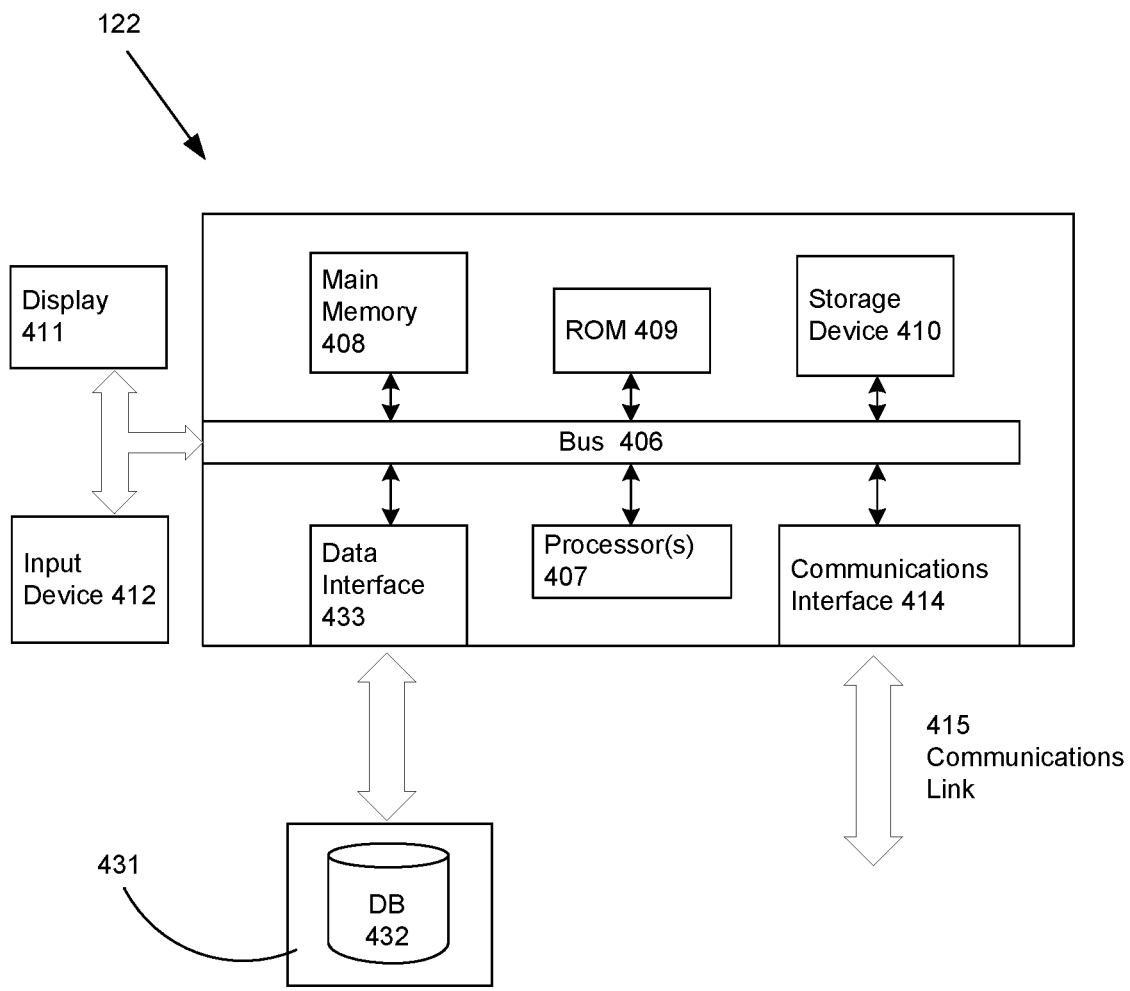
FIG. 4 depicts an embodiment of a data processing system of the present system and method.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

FIG. 1 depicts an overview diagram of an embodiment of a system and method of advanced communication 100. A system and method of advanced communication 100 can comprise a user interface device 102, which can further comprise at least one adjustment assembly 104, sensors 106, and a lip-reading unit 108. An adjustment assembly 104 can be connected to and adjustably positioned within a user interface device 102. An adjustment assembly 104 can further comprise one or more piezo-electric elements 110 and at least one electromechanical drive unit 112. A lip-reading unit 108 can be attached to an adjustment assembly 104 and/or to a user interface device 102.

A user interface device 102 can be electronically connected to a data processing system 114. In such embodiments, sensors 106 on a user interface device 102 can detect parameters such as, but not limited to, auditory, visual, and haptic inputs via piezoelectrics, cameras, microphones, thermometers, or any other known and/or convenient device. In some embodiments, sensors 106 can electronically connect with one another and transmit data to a remote data processing system 114 for decoding from a sensor signal and interpretation into a communication. Sensors 106 can connect with each other and a remote data processing system via wireless networking or any other known and/or convenient system.

In some embodiments, piezoelectric sensors can detect facial movement, interaction force between a user interface device and a user, pressure, or any other known and/or desired parameter. These physical or haptic data can be expressed as an electronic signal that can be transmitted to a data processing system 114. In other embodiments, a video camera can detect visual inputs, such as facial movements, eye movements, and lip motion during speech. These visual inputs can be coded into electronic signals that can be transmitted to a data processing system 114. In other embodiments, an auditory reception device, such as, but not limited to a microphone can detect sound waves generated by a user or the surrounding environment. These auditory inputs can be coded into electronic signals that can be transmitted to a data processing system 114.

A data processing system 114 can comprise a at least one node 116, a cloud component 118, at least one remote location 120, a customized computer hardware system 122, and can be wirelessly connected to at least one other entity 124 besides a user 126. A data processing system 114 can include a computer, mobile device, web-based application, mobile app and/or any other known and/or convenient communication method, device, and/or system. A customized computer hardware system 122 can decode incoming signals from sensors 106 via software, such as, but not limited to that for lip reading, video decoding, audio decoding, and piezoelectric signal decoding. After decoding, a data processing system can wirelessly transmit interpreted signals to at least one node 116, a cloud component, a user 126, and other entities 124. Other entities 124 can likewise send signals to a data processing system 114 via sensors 106 on user interface devices 102. In such embodiments, a user 126 can use visual, auditory, and/or haptic signals to communicate with other entities 124 remotely. In some embodiments, such communications can be conducted in a non-verbal, substantially silent manner.

FIG. 2 depicts a side view of an embodiment of a user interface device 102 in the present system and method. A user interface device 102 and its components can be made of a polymer, metal, ceramic, or any other known and/or convenient material and can be fabricated via casting, molding, or any other known and/or convenient method. In some embodiments, a base component 202 can be configured to fit partially or completely over a user's face, but in other embodiments can comprise an open-frame configuration, eyewear, or any other known and/or convenient configuration. In some embodiments, a base component 202 can be comprised partially or substantially completely of a breathable or porous material. In some embodiments, a bast component can comprise an open-frame configuration. A base component 202 can be positioned on a user by a trolley, hoist, winch, lift, crane, skewer, shim, jack, gear mechanism and/or any known and/or convenient mechanism. As shown in the embodiment of FIG. 2, a base component 202 can contain and/or support at least one adjustment assembly 104, sensors 106, a lip-reading unit 108, and at least one actuating unit 204, but in other embodiments can include any other known and/or convenient devices.

Sensors 106 can be configured to detect eye movement, temperature, pressure, force, light, depth, facial movement and expressions, brain waves, pheromones, electrical current, lip movement or any other known and/or convenient verbal or non-verbal communication indicator. Sensors 106 can translate physical input data to an electronic signal via video coding, audio coding, piezoelectric coding, or any other known and/or convenient process. Electronic signals can be wirelessly transmitted to a data processing system 114 where a signal can be decoded, interpreted, and distributed to a network of other entities 124. A computer system 122 incorporated into a data processing system can operate decoding and translation software configured to each type of input and related signal.

Sensors 106 can be placed on, in, or proximal to any known and/or convenient location on a user interface 102. In some embodiments, sensors 106 configured for video detection and signal transmission can be placed in front of a user's mouth to detect lip movement corresponding to speech, but in other embodiments can be placed in any other known and/or convenient position on a user interface device 102. In some embodiments, sensors 106 configured for video detection and signal transmission can be placed proximal to a user's eyes to detect eye movement. In such embodiments, movement of eyeballs and related anatomical structures, such as, but not limited to eyelids can be detected as a non-verbal form of communication. In other embodiments, sensors 106 configured for video detection and signal transmission can be placed proximal to various locations on a user's face to detect movement of facial muscles in non-verbal expressions.

In some embodiments, sensors 106 configured to detect sound wave data can be placed proximal to a user's mouth to detect verbal signals at very low volume, breath sounds, and/or air movement emanating from a user's mouth. As sound waves are pressure waves, piezoelectric sensors can also be configured to detected changes in pressure from air movement proximal to a user's mouth.

In some embodiments, sensors 106 configured to detect changes in pressure and/or force can be placed proximal to any known and/or convenient position on a user's face or head to detect movement and/or contact force between a user and a user interface device. In such embodiments, piezoelectric devices can be configured to transform physical input into an electronic signal that can provide feedback to an adjustment assembly within a user interface device 102 to improve fit and comfort.

In some embodiments, sensors 106 can be configured to detect electrical brain activity can be placed proximal to specific brain regions to detect electrical activity associated with specific functions. In such embodiments, the level, duration, and location of detected electrical brain activity can be translated into an electrical signal that can be transmitted to other entities 124 after being sent to a data processing system 114. In other embodiments, sensors 106 can use functional near infrared spectroscopy (fNIRS) to detect oxygenation and hemodynamic activity related to brain activity.

FIG. 3 depicts a side view of an embodiment of an adjustment assembly 104. As shown in FIG. 3, an adjustment assembly 104 can comprise one or more piezoelectric elements 110 and at least one electromechanical drive unit 112, which can be connected to a piezoelectric element 110 via a support member 302. An adjustment assembly 104 can also comprise an interface component 304 that can be in substantially direct contact with a user. Piezoelectric elements 110 and electromechanical drive units 112 can be positionable in relation to each other. Electromechanical drive units 112 can incorporate motor, screw or any other known and/or convenient mechanisms and can be made of metal, plastic and/or any other known and/or convenient material.

A lip-reading unit 108 can incorporate video, sensory implant and any known and/or future lip-reading technology. In some embodiments, a lip-reading unit 108 can be operated/controlled remotely through a computer, a mobile device, through a web-based application, through a mobile app and/or any other known or future communication system. A lip-reading unit 108 can be operated remotely via sensors 106 coupled with any other user interface device 102. Each lip-reading unit 108 can work independently or in coordination with one or more other systems whether managed manually, automatically, semi-automatically, machine learning, artificial intelligence and/or in any combination. Related software to interpret input from a lip-reading unit 108, such as, but not limited to LipNet can be executed on a computer system 122 as part of a data processing system 114.

As a non-limiting example in such embodiments, LipNet (see: www.arXiv:01599v2 [cs.LG] 16 Dec. 2016) provides a model for end-to-end sentence lipreading. LipNet "maps a variable-length sequence of video frames to text, making use of spatiotemporal convolutions, a recurrent network, and the connectionist temporal classification loss, trained entirely end-to-end." This model can map sequences of video image frames to entire phrases and sentences. As a user speaks or silently dictates a word, phrase, or sentence, the LipNet model processes the video frame sequence and translates it into a text sequence. In the present system and method, a text sequence can then be translated into an electrical signal to be transmitted wireless through a network.

In some embodiments, at least one electromechanical drive unit 112 can include a screw drive system, which can allow a user to make coarse adjustments to the positioning of a user interface device 102, but in other embodiments can employ any other known and/or convenient mechanism. A user can also make fine adjustments with one or more piezoelectric elements 110 or any other known and/or convenient device. In some embodiments, sensors 106 can provide feedback to electromechanical drive units 112 or piezoelectric elements 110 to make fine adjustments to fit, position, or any other known and/or convenient parameter.

FIG. 4 depicts a schematic diagram of a computer system 122. The execution of the sequences of instructions required to practice the embodiments can be performed by a computer system 122 as shown in FIG. 4. In an embodiment, execution of the sequences of instructions is performed by a single computer system 122. According to other embodiments, two or more computer systems 122 coupled by a communication link 415 can perform the sequence of instructions in coordination with one another. Although a description of only one computer system 122 will be presented below, however, it should be understood that any number of computer systems 122 can be employed to practice the embodiments.

A computer system 122 according to an embodiment will now be described with reference to FIG. 4, which is a block diagram of the functional components of a computer system 122. As used herein, the term computer system 122 is broadly used to describe any computing device that can store and independently run one or more programs.

Each computer system 122 can include a communication interface 414 coupled to the bus 406. The communication interface 414 provides two-way communication between computer systems 122. The communication interface 414 of a respective computer system 122 transmits and receives electrical, electromagnetic or optical signals, that include data streams representing various types of signal information, e.g., instructions, messages and data. A communication link 415 links one computer system 122 with another computer system 122. For example, the communication link 415 can be a LAN, in which case the communication interface 414 can be a LAN card, or the communication link 415 can be a PSTN, in which case the communication interface 414 can be an integrated services digital network (ISDN) card or a modem, or the communication link 415 can be the Internet, in which case the communication interface 414 can be a dial-up, cable or wireless modem.

A computer system 122 can transmit and receive messages, data, and instructions, including program, i.e., application, code, through its respective communication link 415 and communication interface 414. Received program code can be executed by the respective processor(s) 407 as it is received, and/or stored in the storage device 410, or other associated non-volatile media, for later execution.

In an embodiment, the computer system 122 operates in conjunction with a data storage system 431, e.g., a data storage system 431 that contains a database 432 that is readily accessible by the computer system 122. The computer system 122 communicates with the data storage system 431 through a data interface 433. A data interface 433, which is coupled to the bus 406, transmits and receives electrical, electromagnetic or optical signals, that include data streams representing various types of signal information, e.g., instructions, messages and data. In embodiments, the functions of the data interface 433 can be performed by the communication interface 414.

Computer system 122 includes a bus 406 or other communication mechanism for communicating instructions, messages and data, collectively, information, and one or more processors 407 coupled with the bus 406 for processing information. Computer system 122 also includes a main memory 408, such as a random access memory (RAM) or other dynamic storage device, coupled to the bus 406 for storing dynamic data and instructions to be executed by the processor(s) 407. The main memory 408 also can be used for storing temporary data, i.e., variables, or other intermediate information during execution of instructions by the processor(s) 407.

The computer system 122 can further include a read only memory (ROM) 409 or other static storage device coupled to the bus 406 for storing static data and instructions for the processor(s) 407. A storage device 410, such as a magnetic disk or optical disk, can also be provided and coupled to the bus 406 for storing data and instructions for the processor(s) 407.

A computer system 122 can be coupled via the bus 406 to a display device 411, such as, but not limited to, a cathode ray tube (CRT) or a liquid-crystal display (LCD) monitor, for displaying information to a user. An input device 412, e.g., alphanumeric and other keys, is coupled to the bus 406 for communicating information and command selections to the processor(s) 407.

According to one embodiment, an individual computer system 122 performs specific operations by their respective processor(s) 407 executing one or more sequences of one or more instructions contained in the main memory 408. Such instructions can be read into the main memory 408 from another computer-usable medium, such as the ROM 409 or the storage device 410. Execution of the sequences of instructions contained in the main memory 408 causes the processor(s) 407 to perform the processes described herein. In alternative embodiments, hard-wired circuitry can be used in place of or in combination with software instructions. Thus, embodiments are not limited to any specific combination of hardware circuitry and/or software.

The term "computer-usable medium," as used herein, refers to any medium that provides information or is usable by the processor(s) 407. Such a medium can take many forms, including, but not limited to, non-volatile, volatile and transmission media. Non-volatile media, i.e., media that can retain information in the absence of power, includes the ROM 409, CD ROM, magnetic tape, and magnetic discs. Volatile media, i.e., media that can not retain information in the absence of power, includes the main memory 408. Transmission media includes coaxial cables, copper wire and fiber optics, including the wires that comprise the bus 406. Transmission media can also take the form of carrier waves; i.e., electromagnetic waves that can be modulated, as in frequency, amplitude or phase, to transmit information signals. Additionally, transmission media can take the form of acoustic or light waves, such as those generated during radio wave and infrared data communications.

In the foregoing specification, the embodiments have been described with reference to specific elements thereof. It will, however, be evident that various modifications and changes can be made thereto without departing from the broader spirit and scope of the embodiments. For example, the reader is to understand that the specific ordering and combination of process actions shown in the process flow diagrams described herein is merely illustrative, and that using different or additional process actions, or a different combination or ordering of process actions can be used to enact the embodiments. The specification and drawings are, accordingly, to be regarded in an illustrative rather than restrictive sense.

It should also be noted that the present invention can be implemented in a variety of computer systems. The various techniques described herein can be implemented in hardware or software, or a combination of both. Preferably, the techniques are implemented in computer programs executing on programmable computers that each include a processor, a storage medium readable by the processor (including volatile and non-volatile memory and/or storage elements), at least one input device, and at least one output device. Program code is applied to data entered using the input device to perform the functions described above and to generate output information. The output information is applied to one or more output devices. Each program is preferably implemented in a high-level procedural or object-oriented programming language to communicate with a computer system. However, the programs can be implemented in assembly or machine language, if desired. In any case, the language can be a compiled or interpreted language. Each such computer program is preferably stored on a storage medium or device (e.g., ROM or magnetic disk) that is readable by a general or special purpose programmable computer for configuring and operating the computer when the storage medium or device is read by the computer to perform the procedures described above. The system can also be considered to be implemented as a computer-readable storage medium, configured with a computer program, where the storage medium so configured causes a computer to operate in a specific and predefined manner. Further, the storage elements of the exemplary computing applications can be relational or sequential (flat file) type computing databases that are capable of storing data in various combinations and configurations.

Figure 5:
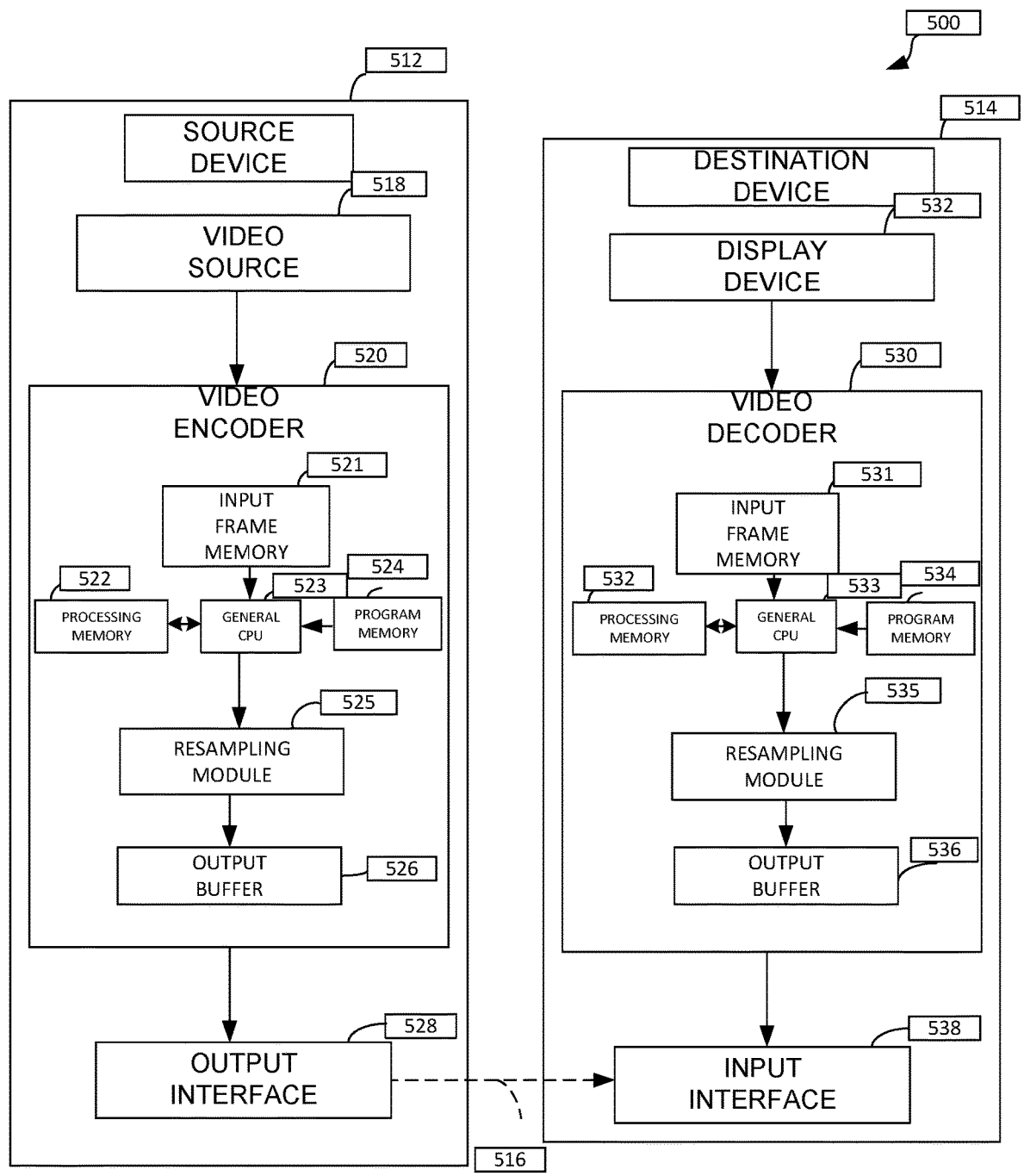
FIG. 5 is a high-level view of a source input and coding device and a destination recipient and decoding device for use in the present system and method.

FIG. 5 is a high-level view of a source device 512 and destination device 510 that may incorporate features of the systems and devices described herein. As shown in FIG. 5, example video coding system 510 includes a source device 512 and a destination device 514 where, in this example, the source device 512 generates encoded video data. Accordingly, source device 512 may be referred to as a video encoding device. Destination device 514 may decode the encoded video data generated by source device 512. Accordingly, destination device 514 may be referred to as a video decoding device. Source device 512 and destination device 514 may be examples of video coding devices.

Destination device 514 may receive encoded video data from source device 512 via a channel 516. Channel 516 may comprise a type of medium or device capable of moving the encoded video data from source device 512 to destination device 514. In one example, channel 516 may comprise a communication medium that enables source device 512 to transmit encoded video data directly to destination device 514 in real-time.

In this example, source device 512 may modulate the encoded video data according to a communication standard, such as a wireless communication protocol, and may transmit the modulated video data to destination device 514. The communication medium may comprise a wireless or wired communication medium, such as a radio frequency (RF) spectrum or one or more physical transmission lines. The communication medium may form part of a packet-based network, such as a local area network, a wide-area network, or a global network such as the Internet. The communication medium may include routers, switches, base stations, or other equipment that facilitates communication from source device 512 to destination device 514. In another example, channel 516 may correspond to a storage medium that stores the encoded video data generated by source device 512.

In the example of FIG. 5, source device 512 includes a video source 518, video encoder 520, and an output interface 522. In some cases, output interface 528 may include a modulator/demodulator (modem) and/or a transmitter. In source device 512, video source 518 may include a source such as a video capture device, e.g., a video camera, a video archive containing previously captured video data, a video feed interface to receive video data from a video content provider, and/or a computer graphics system for generating video data, or a combination of such sources.

Video encoder 520 may encode the captured, pre-captured, or computer-generated video data. An input image may be received by the video encoder 520 and stored in the input frame memory 521. The general purpose processor 523 may load information from here and perform encoding. The program for driving the general purpose processor may be loaded from a storage device, such as the example memory modules depicted in FIG. 5. The general purpose processor may use processing memory 522 to perform the encoding, and the output of the encoding information by the general processor may be stored in a buffer, such as output buffer 526.

The video encoder 520 may include a resampling module 525 which may be configured to code (e.g., encode) video data in a scalable video coding scheme that defines at least one base layer and at least one enhancement layer. Resampling module 525 may resample at least some video data as part of an encoding process, wherein resampling may be performed in an adaptive manner using resampling filters.

The encoded video data, e.g., a coded bit stream, may be transmitted directly to destination device 514 via output interface 528 of source device 512. In the example of FIG. 5, destination device 514 includes an input interface 538, a video decoder 530, and a display device 532. In some cases, input interface 528 may include a receiver and/or a modem. Input interface 538 of destination device 514 receives encoded video data over channel 516. The encoded video data may include a variety of syntax elements generated by video encoder 520 that represent the video data. Such syntax elements may be included with the encoded video data transmitted on a communication medium, stored on a storage medium, or stored a file server.

The encoded video data may also be stored onto a storage medium or a file server for later access by destination device 514 for decoding and/or playback. For example, the coded bitstream may be temporarily stored in the input buffer 531, then loaded in to the general purpose processor 533. The program for driving the general-purpose processor may be loaded from a storage device or memory. The general-purpose processor may use a process memory 532 to perform the decoding. The video decoder 530 may also include a resampling module 535 similar to the resampling module 525 employed in the video encoder 520.

FIG. 5 depicts the resampling module 535 separately from the general purpose processor 533, but it would be appreciated by one of skill in the art that the resampling function may be performed by a program executed by the general purpose processor, and the processing in the video encoder may be accomplished using one or more processors. The decoded image(s) may be stored in the output frame buffer 536 and then sent out to the input interface 538.

Display device 538 may be integrated with or may be external to destination device 514. In some examples, destination device 514 may include an integrated display device and may also be configured to interface with an external display device. In other examples, destination device 514 may be a display device. In general, display device 538 displays the decoded video data to a user.

Video encoder 520 and video decoder 530 may operate according to a video compression standard. ITU-T VCEG (Q6/16) and ISO/IEC MPEG (JTC 1/SC 29/WG 11) are studying the potential need for standardization of future video coding technology with a compression capability that significantly exceeds that of the current High Efficiency Video Coding HEVC standard (including its current extensions and near-term extensions for screen content coding and high-dynamic-range coding). The groups are working together on this exploration activity in a joint collaboration effort known as the Joint Video Exploration Team (JVET) to evaluate compression technology designs proposed by their experts in this area. A recent capture of JVET development is described in the "Algorithm Description of Joint Exploration Test Model 5 (JEM 5)", JVET-E1001-V2, authored by J. Chen, E. Alshina, G. Sullivan, J. Ohm, J. Boyce.

Additionally or alternatively, video encoder 520 and video decoder 530 may operate according to other proprietary or industry standards that function with the disclosed JVET features. Thus, other standards such as the ITU-T H.264 standard, alternatively referred to as MPEG-4, Part 10, Advanced Video Coding (AVC), or extensions of such standards. Thus, while newly developed for JVET, techniques of this disclosure are not limited to any particular coding standard or technique. Other examples of video compression standards and techniques include MPEG-2, ITU-T H.263 and proprietary or open source compression formats and related formats.

Video encoder 520 and video decoder 530 may be implemented in hardware, software, firmware or any combination thereof. For example, the video encoder 520 and decoder 530 may employ one or more processors, digital signal processors (DSPs), application specific integrated circuits (ASICs), field programmable gate arrays (FPGAs), discrete logic, or any combinations thereof. When the video encoder 520 and decoder 530 are implemented partially in software, a device may store instructions for the software in a suitable, non-transitory computer-readable storage medium and may execute the instructions in hardware using one or more processors to perform the techniques of this disclosure. Each of video encoder 520 and video decoder 530 may be included in one or more encoders or decoders, either of which may be integrated as part of a combined encoder/decoder (CODEC) in a respective device.

Aspects of the subject matter described herein may be described in the general context of computer-executable instructions, such as program modules, being executed by a computer, such as the general-purpose processors 523 and 533 described above. Generally, program modules include routines, programs, objects, components, data structures, and so forth, which perform particular tasks or implement particular abstract data types. Aspects of the subject matter described herein may also be practiced in distributed computing environments where tasks are performed by remote processing devices that are linked through a communications network. In a distributed computing environment, program modules may be located in both local and remote computer storage media including memory storage devices.

Examples of memory include random access memory (RAM), read only memory (ROM), or both. Memory may store instructions, such as source code or binary code, for performing the techniques described above. Memory may also be used for storing variables or other intermediate information during execution of instructions to be executed by a processor, such as processor 523 and 533.

A storage device may also store instructions, instructions, such as source code or binary code, for performing the techniques described above. A storage device may additionally store data used and manipulated by the computer processor. For example, a storage device in a video encoder 520 or a video decoder 530 may be a database that is accessed by computer system 523 or 533. Other examples of storage device include random access memory (RAM), read only memory (ROM), a hard drive, a magnetic disk, an optical disk, a CD-ROM, a DVD, a flash memory, a USB memory card, or any other medium from which a computer can read.

A memory or storage device may be an example of a non-transitory computer-readable storage medium for use by or in connection with the video encoder and/or decoder. The non-transitory computer-readable storage medium contains instructions for controlling a computer system to be configured to perform functions described by particular embodiments. The instructions, when executed by one or more computer processors, may be configured to perform that which is described in particular embodiments.

Also, it is noted that some embodiments have been described as a process which can be depicted as a flow diagram or block diagram. Although each may describe the operations as a sequential process, many of the operations can be performed in parallel or concurrently. In addition, the order of the operations may be rearranged. A process may have additional steps not included in the figures.

Figure 6:
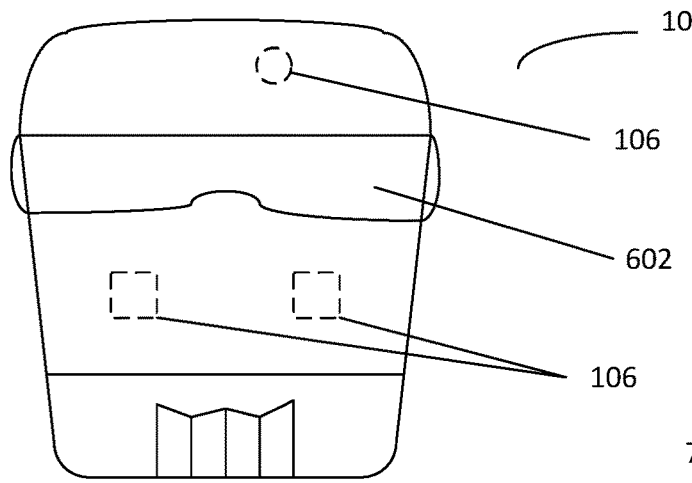
FIG. 6 depicts a front view of an alternate embodiment of a user interface in the present system and method.

Particular embodiments may be implemented in a non-transitory computer-readable storage medium for use by or in connection with the instruction execution system, apparatus, system, or machine. The computer-readable storage medium contains instructions for controlling a computer system to perform a method described by particular embodiments. The computer system may include one or more computing devices. The instructions, when executed by one or more computer processors, may be configured to perform that which is described in particular embodiments FIG. 6 depicts an alternative embodiment of a user interface device 102 in the present system and method. In the embodiment shown in FIG. 6, a user interface device 102 can further comprise a visual unit 602. In some embodiments, a visual unit 602 can be operated remotely via sensors 106 that can be coupled with other user interface devices 102 used by other entities 124. In such embodiments, sensors 106 can be configured to detect visual signals originating internal to a user interface device 102 (e.g., facial movement), or externally (e.g., the surrounding environment). A visual unit 602 can display content inward, toward the user, or outward, away from the user via a liquid crystal display (LCD) or any other known and/or convenient interface. In some embodiments, sensors 106 can be configured to coordinate, guide and/or manage the movements of a visual unit 602. By way of non-limiting example, sensors 106 configured to detect position can send feedback to an adjustment mechanism 104 to adjust the position of a visual unit 602. In some embodiments, sensors 106 and a visual unit 602 can be operated and/or controlled via computer, mobile device, web-based application, mobile app and/or any other known or convenient communication system. In operation, sensors 106 can collect other data, such as, but not limited to temperature and other environmental conditions, which can then be sent to a data processing unit 714. An onboard data processing unit 714 can interpret the data and can then display the data in visual form on a visual unit 602. In the non-limiting example of temperature detection, a measured temperature can be displayed as an alphanumeric digital display.

Figure 7:
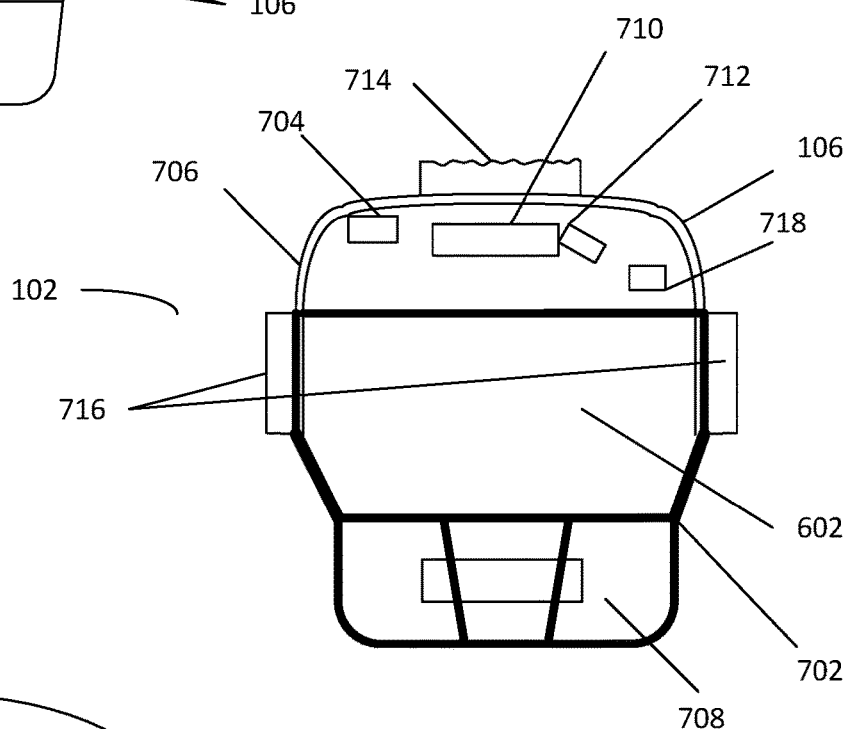
FIG. 7 depicts an alternate embodiment of a user interface device for use in the present system and method.

FIG. 7 depicts an alternate embodiment of a user interface device 102 for use in the present system and method. In the embodiment shown in FIG. 7, the user interface device 102 can comprise a frame and attachment unit 702, an environmental control unit 704, a wearable item 706, a communication unit 708, an energy harvesting unit 710, an actuating mechanism 712, a data processing unit 714, an audio unit 716, a haptic unit 718, and sensors 106.

As shown in the embodiment of FIG. 7, a wearable item 706 can be headwear, such as, but not limited to a helmet or cap, but in other embodiments can be any other known and/or convenient item, equipment, and/or garment. In some embodiments, a frame and attachment unit 702 can be coupled with any known and/or convenient wearable item 706 via any known and/or convenient attachment mechanism including, but not limited to, adhesive, screws, anchors, drilling, and/or implanting stable attachments inside a user. In some embodiments, a wearable item 706 and a frame and attachment unit 702 can be interchangeable, but in other embodiments can be configured to selectively engage with one another.

A frame and attachment unit 702 can have a substantially rounded, orthogonal, or any other known and/or convenient geometry. In some embodiments, a frame and attachment unit 702 can be configured to fit over a user's face. A frame and attachment unit 702 can be comprised of metal, polymer, ceramic, or any other known and/or convenient material.

An environmental control unit 704 can comprise heating and/or cooling units, which can be mechanical, electrical, thermo-electric, and/or any known and/or convenient devices. In some embodiments, an environmental control unit 704 can be in electronic communication with sensors 106 in a user interface device 102 to provide control feedback, but in other embodiments can be controlled remotely. In some embodiments, sensors 106 can be configured to detect temperature in the space between a user interface 102 device and a user's face. In such embodiments, a temperature sensor 106 can send an electrical signal to an environmental control unit 704, which can include a switch to activate a heating/cooling unit. As a non-limiting example, a cooling unit, such as, but not limited to a thermoelectric device or mechanical fan can be activated at a desired temperature.

In some embodiments, a communication unit 708 can comprise a speaker and/or microphone and/or any known and/or convenient audio recording, transmitting, or receiving device. In some embodiments, a communication unit 708 can transmit to a remote processing system 114 to be transmitted to a network of other users and/or an onboard processing unit 714. In some embodiments, a communication unit 708 can have microphone to detect verbal input. In such embodiments, a microphone can transform a detected sound signal into an electrical signal, which can be sent to a remote processing system 114 to be transmitted to a network of other users and/or an onboard processing unit 714 for recording or transmission. In some embodiments, a speaker can further comprise a receiver unit to receive transmissions of electrical audio signals from other remote users. In such embodiments, a user can hear audio transmissions from other users, such as spoken communications.

An energy harvesting unit 710 can comprise energy harvesting processes including, but not limited to, a solar, thermal, wind, kinetic, and/or any other known and/or convenient energy harvesting process. In some embodiments, an actuating device 712 can position an energy harvesting unit 710 in any desirable direction and/or configuration for convenience and/or to optimize performance. By way of nonlimiting example, an energy harvesting unit 710 can comprise a photovoltaic panel. In such embodiments, an actuating device can position a panel for optimal solar energy collection.

An onboard data processing unit 714 can receive input from sensors 106 and/or a communication unit 708 and be connected to or integrated with a wearable item 706. In other embodiments, an onboard data processing unit can be connected to or integrated with a frame and attachment unit 702. In some embodiments, an onboard data processing unit 714 can be in electrical communication with an environmental control unit 704, a communication unit 708, an energy harvesting unit 710, and actuating device 712, an audio unit 716, and any other known and/or convenient components of a user interface device 102. In some embodiments, an onboard processing unit 714 can receive input from sensors 106, decode the input and transform it into an electrical signal to be sent to a remote processing unit 114.

An audio unit 716 can record and/or listen to auditory signals of a user or a surrounding environment and send auditory data to a data processing unit 714. An audio unit can transmit and control traditional audio from sensors 106 placed in any location on a user interface device 102. In some embodiments, and audio unit 716 can be electronically connected to a communication unit 708.

In some embodiments, a haptic unit 718 can receive input from sensors 106, signals from a remote processing unit 114, a visual unit 602, a communication unit, or any other known and/or convenient device. In such embodiments, a haptic unit 718 can translate a signal into a vibration, touch, or any other known and/or convenient haptic signal that can be felt by a user. In some embodiments, a haptic unit can be located proximal to the forehead of a user, but in other embodiments, can be positioned proximal to a cheek, chin, neck, scalp, or any other known and/or convenient location.

Figure 8:
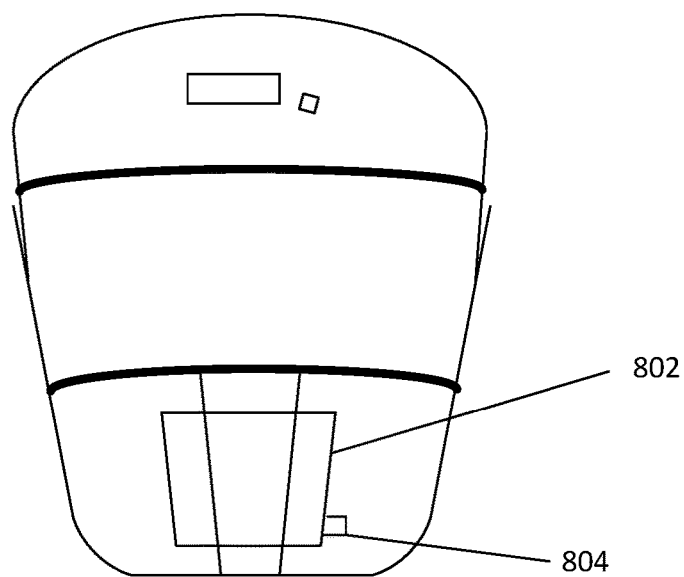
FIG. 8 depicts an alternate embodiment of a user interface device for use in the system and method.

FIG. 8 depicts an alternate embodiment of a user interface device 102 for use in the present system and method that can further comprise an oral containment unit 802 and an actuating device 804. In some embodiments, an oral containment unit 802 can comprise any known solid or perforated fabric or any known and/or convenient material. In other embodiments, an oral containment unit 802 can comprise a frame configuration. An oral containment unit 802 can restrict the mouth or tongue, restrict and/or cancel noise, contain filters, contain sensory response interfaces, and/or perform any other known and/or convenient function.

FIG. 9 depicts an alternative embodiment with lip-reading sensors 902 in an alternate configuration. In some embodiments, lip-reading sensors 902 can be placed above, below, laterally, or in any other known and/or convenient position relative to a user's lips. In such embodiments an onboard data processing unit 714 and/or a data processing unit 114 can execute additional software to translate lip motion from an alternate perspective.

FIGS. 10a-10c depict various views of an alternative embodiment of the present system and method further comprising an oral containment unit 802.

The component of the user interface device 102 shown in FIG. 10a, can comprise a frame and attachment unit 1002, an oral containment unit 802, a sensor 106, an energy harvesting unit 710, and an actuating device 712. A frame and attachment unit 1002 can have a hinge 1004 and/or any known and/or convenient attachment to a user interface device 102 in order for an oral containment unit 802 to open to either side or up and down, or any other known and/or convenient movement.

In operation, an energy harvesting unit 710 can provide power for sensors 106 that can send signals to a frame and attachment unit 1002 with instructions to close an oral containment unit 802 over a frame and attachment unit 1002. Sensors 106 can be controlled locally or remotely in order to control the opening, closing, and activation of any feature of an oral containment unit 802.

FIG. 10b depicts the component of a user interface device 102 in FIG. 10a in a closed position. In operation, a frame and attachment unit 1002 can couple the user interface device 102 with an oral containment unit 802 and an actuating device 1004. An oral containment unit 802 can conceal verbal and nasal noise, facial expressions and/or another known non-desirable expressions. An actuating device 1004 can also be positioned to potentially conceal any undesired/unintended expression.

FIG. 10c depicts the component of the user interface device 102 with a filter 1006 installed behind an oral containment unit 802. A filter 1006 can be made of charcoal, polymer, textile, and/or any other known or convenient material.

Figure 11:
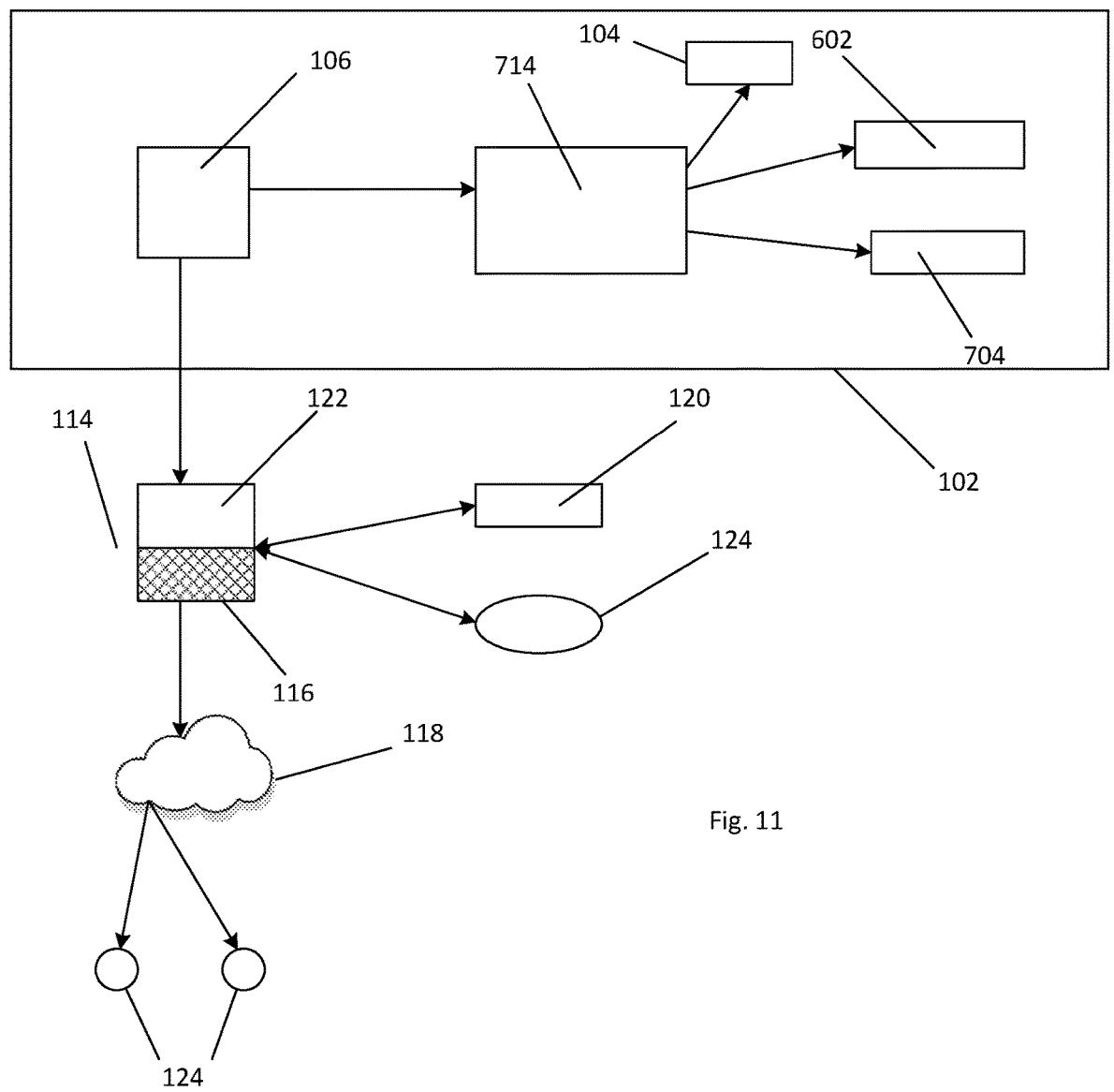
FIG. 11 depicts a schematic diagram of an embodiment of the present system and method in use.

FIG. 11 depicts an alternative embodiment of the present system and method in which a user interface device 102 can include and communicate with an onboard data processing unit 714. Sensors 106 on a user interface device can send signals to an onboard data processing unit 714 and/or a remote data processing unit. In operation, a user can place a user interface device 102 in proximity of the face and sensors 106 can send signals to an adjustment assembly 104 to adjust the position of a user interface device 102 in relation to sensors 106 on a wearer of a user interface device 102. Sensors 106 can send signals based on eye movement, temperature, depth, expressions, lip movement and/or any other known or convenient verbal or non-verbal communication to an onboard data processor 714. An onboard data processor 714 and/or a remote data processor 114 can read signals sent from sensors 106 to interpret the needs and/or requests of a user of a user interface device 102. By way of non-limiting example, a sensor 106 can be configured to detect eye movement in a particular direction as a non-verbal communication. In such embodiments, a sensor 106 can detect eye movement and send a signal corresponding to the direction of movement to an onboard processing unit 714 or directly to a remote processing unit 114. A signal can be interpreted and transformed into an electrical wireless signal by a remote processor 114 and sent to other users 124 across a wireless network, which can include a cloud 118 component. Other user interface devices 102 can receive an electrical signal and present it to a user as an auditory, visual, or haptic signal.

Figure 12:
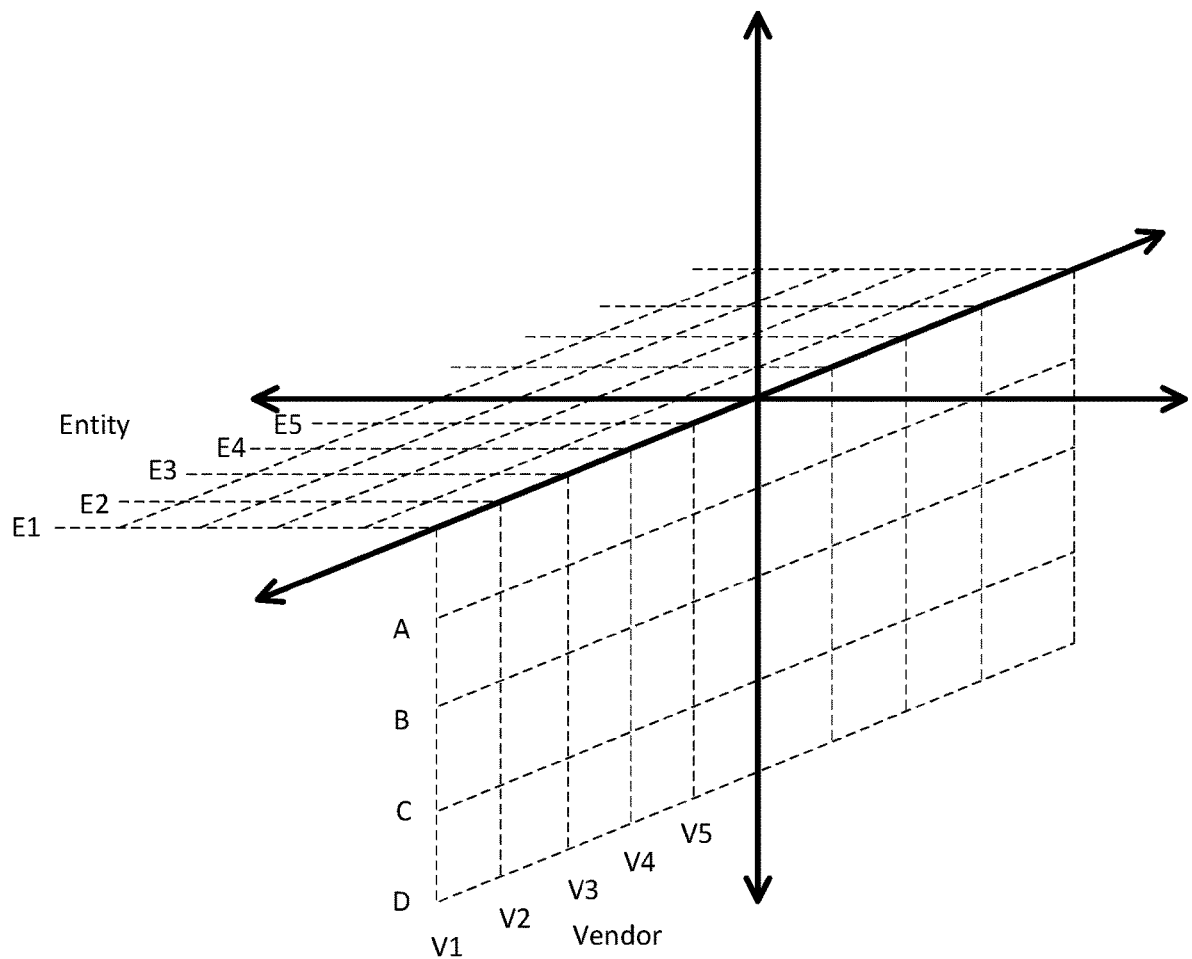
FIG. 12 depicts a schematic diagram of an embodiment of the present system and method in use.

FIG. 12 depicts an alternate embodiment of the present system and method. In the embodiment show in FIG. 12, a system and method of advanced communication can comprise a user interface device 102, sensors 106 and a remote data processor(s) 114. In operation, sensors 106 on a user interface device 102 can send data to a remote data processor 114. The data processor 114 interprets the data collected by the sensors 106 and then transmits data to one or more user interface devices 102. The data transmitted from one or more user interface devices 102 can include communications including, but not limited to, payment terms, work requests and/or any other known and/or convenient communication iteratively negotiated. Data from a user interface device 102 can be transmitted via computer, mobile device, web-based application, a mobile application, or any other known and/or convenient communication tool.

By way of non-limiting example, a sensor 106 can be configured for auditory input. A user can verbally communicate a work request, and a sensor 106 can send an electrical signal to a remote data processor. A remote data processor 114 can receive and decode the signal and send a communication signal to other users in a wireless network. Other users can receive a communication as an audio, visual, or haptic message via a user interface device 102. Other users can respond to a communication with payment terms, availability, or any other known and convenient information relevant to a work request. The original sender of the request and the other user or users can repeat this process to iteratively reach an agreement for execution of the work request. In other embodiments, sales, trades, and any other known and/or transaction can be conducted in a likewise manner.

Figure 13:
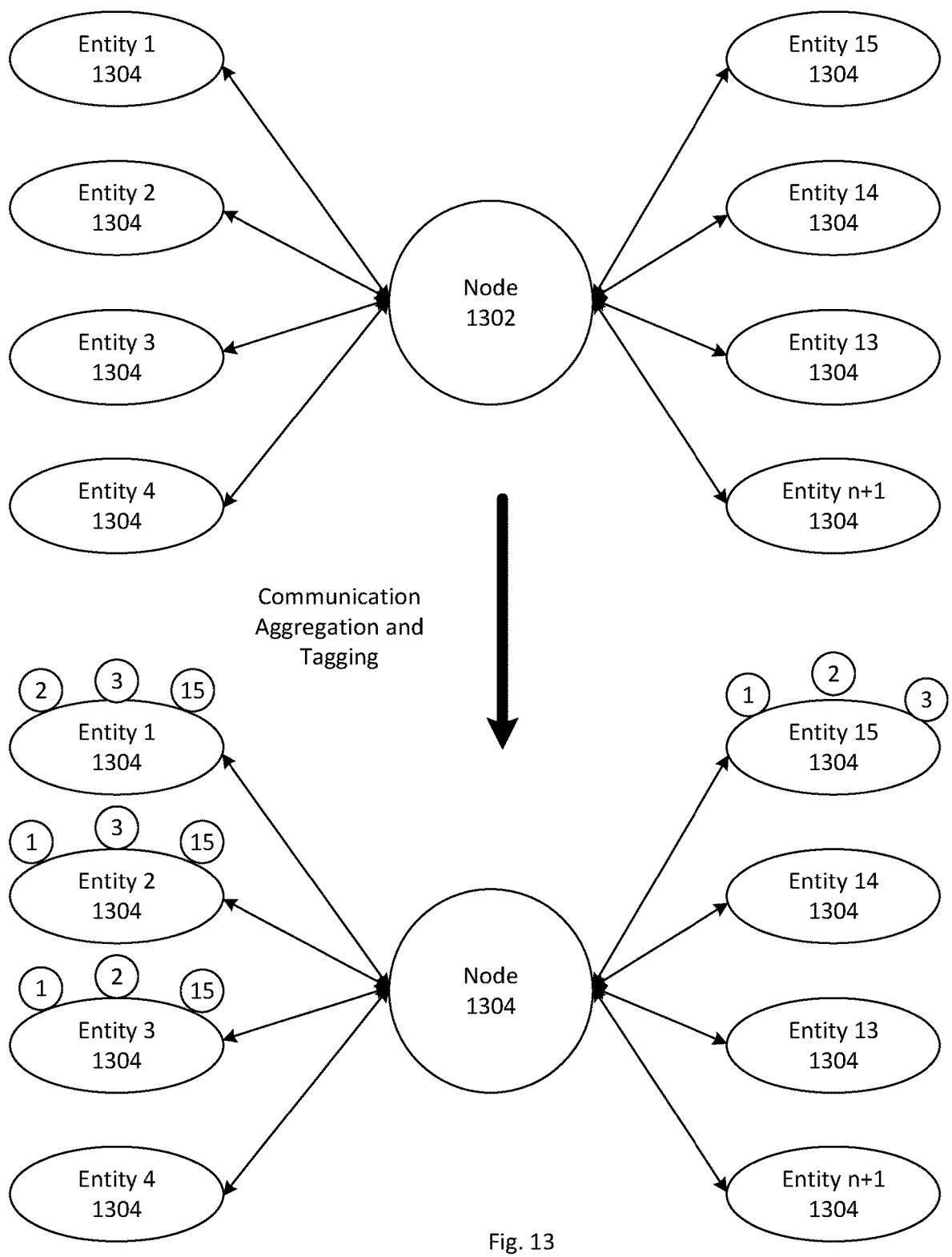
FIG. 13 depicts a schematic diagram of an embodiment of the present system and method in use.

FIG. 13 depicts an embodiment of a method of advanced communication. In the embodiment of a method of advanced communication shown in FIG. 13, a method of advanced communication can comprise a centralized, decentralized, and/or distributed node 1302 on a network, and multiple entities 1304 that can receive and/or send communications to and/or from a node 1302. In some embodiments, one or more entities 1304 can communicate with a node 1302 by sending or receiving signals to and/or from a node 1302. In one embodiment, these communications can be interactions between entities seeking to settle or negotiate terms of payment and/or requests for service or any known and/or convenient communication request.

Figure 14:
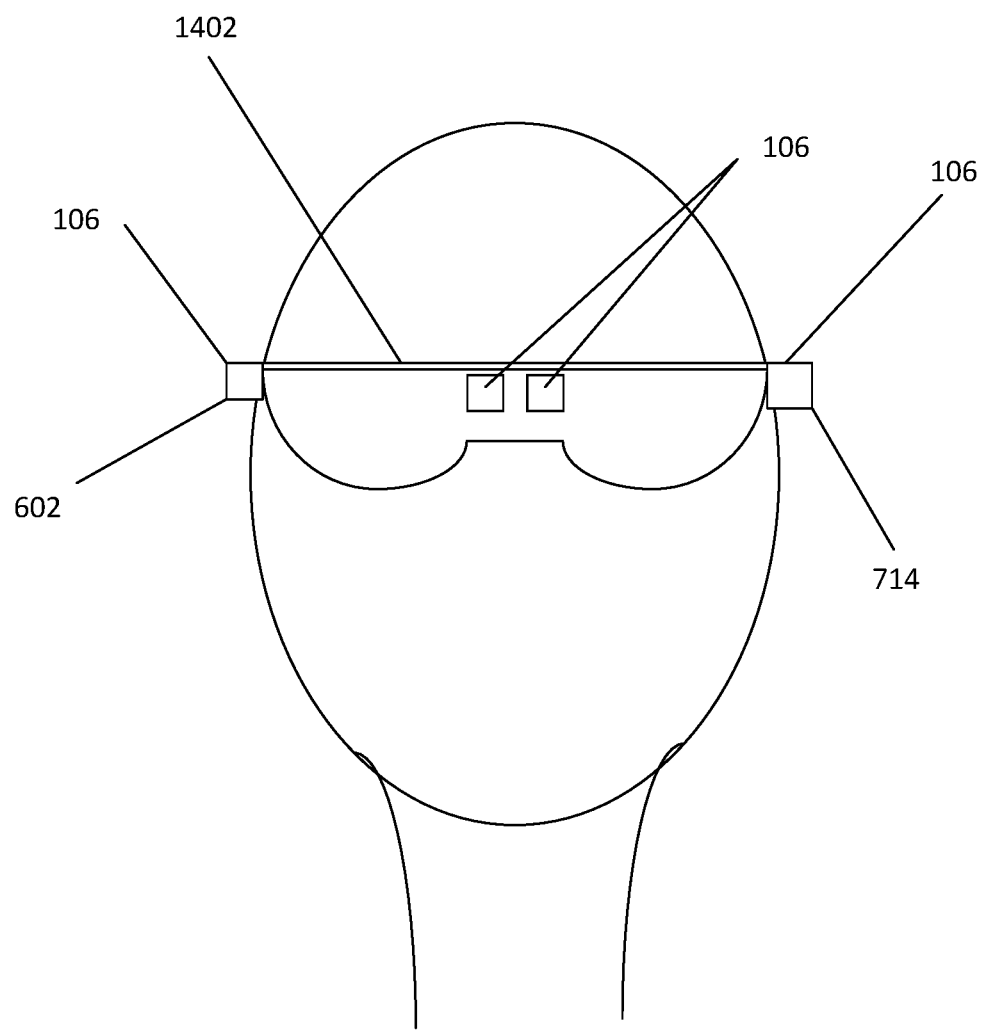
FIG. 14 depicts a front view of alternative embodiment of a user interface device in the present system and method.

FIG. 14 depicts an alternative embodiment of a user interface device 102 in the present system and method. In the embodiment shown, a wearable item 706 can comprise glasses, goggles, or any other known and/or convenient eyewear 1402. In such embodiments, sensors 106 and an onboard data processing unit 714 can be attached to, embedded, or integrated into eyewear 1402. Eyewear 1402 can also include a visual unit 602 that can partially or substantially completely cover the eye region of a user. In some embodiments, eyewear 1402 can be implanted into a user.

In general operation, sensors 106 on a user interface device 102 can transmit data to a data processor 114, an actuating device 712, an environmental control unit 710, a communication unit 708, a visual unit 602, an audio unit 716, a oral containment unit 802, and/or any other known and/or convenient attachment. Data can then be interpreted by a data processor 714 and a user interface device 102 can respond according to the data received. A user can place a user interface device 102 in proximity of the face and piezo-electric elements 304 and motor and/or screw drives 112 can adjust the position of a user interface device 102 in relation to sensors 106 and/or a user's face.

FIG. 15a depicts a schematic chart of the overall sensing, communication, and other functions in the present system and method for advanced communication 100. In some embodiments, a condition, status, event, or any other known and/or convenient situation can be monitored by sensors 106. Sensors 106 can detect indicative parameters, such as, but not limited to force, motion, temperature, humidity, brain wave function, hemodynamic changes, sound waves, and visual input of these conditions. Sensors 106 can transmit data to an onboard processor 714 and/or and a remote processor 114. An onboard processor 714 can collect data and/or respond with a signal to a component of a user interface 102 to make an adjustment, provide feedback to a user, or any other known and/or convenient function. In some embodiments, a remote processor 114 can interpret received data and compare with reference data to make a decision as to a response. In such embodiments, a remote processor 114 can determine a response, the form of a response (audio, visual, or haptic), and send a wireless signal to a user to activate the appropriate component of a user interface device 102. A remote processor 114 can collect data and/or send a signal to another user in a communicative function, such as, but not limited to, audio, visual, or haptic.

In some embodiments, a user interface 102 can have a lip-reading unit 108. In some embodiments a video system can track and/or record lip motion when a user speaks or substantially silently mouths words, but in other embodiments, any known and/or convenient input device may be used. In such embodiments, a video signal can be sent to a processor 114 by the system and method discussed herein. A processor 114 can comprise a computer system 122, which can further comprise lip-motion analysis software, such as, but not limited to, that of LipNet, which provides a model that can map a variable-length sequence of video frames to text (cite: www.arXiv.org/1611.01599). In such embodiments, spatiotemporal visual features and sequences can be used to decode text from the motion of a user's mouth. A processor 114 can send a decoded message to another user via an audio unit 716 and/or a visual unit 602. A processor 114 can also store lip-reading data for documentation and any other known and/or convenient purpose. In such embodiments, a user can communicate substantially silently with other users via lip motion rather than verbal speech. In some embodiments, a containment device 802 can mask a user's lip motion from external view.

In some embodiments, sensors 106 can detect communicative facial movement and expressions. In such embodiments, sensors 106 can be video-input devices, pressure or force sensors (such as, but not limited to piezoelectric sensors), motion detectors, or any other known and/or convenient device. Signals from these sensors can be sent to a remote processor 114 to be decoded into a signal that can be sent to another user. In such embodiments, a decoded signal can be transmitted to an audio unit 716, a visual unit 602, a haptic unit 718 or any other know and/or convenient component of another user's interface device 102. A processor 114 can also save data from original sensor 106 signals and/or decoded signals for documentation or any other known and/or convenient purpose.

In some embodiments, sensors 106 can detect brain activity. In such embodiments, sensors 106 can be electroencephalogram (EEG) sensors, functional near infrared spectroscopy (fNIRS) sensors, temperature and/or humidity sensors, and/or any other known and/or convenient device.

In some embodiments, EEG sensors can detect electrical impulses from specific areas of the brain associated with certain functions. In such embodiments, electrical signals from these sensors 106 can be sent to a remote processor 114 to be decoded into a signal that can be sent to another user. In such embodiments, a decoded signal can be transmitted to an audio unit 718, a visual unit 602, a transcranial direct stimulation unit (TDCS), or any other know and/or convenient component of another user's interface device 102. In embodiments having a TDCS unit, TDCS can apply an electrical signal to a specific region of another user's brain to communicate brain activity signals. A processor 114 can also save data from original sensor 106 signals and/or decoded signals for documentation or any other known and/or convenient purpose.

In some embodiments, fNIRS can use selected near-infrared waves to measure hemodynamic changes in regions of the brain. In such embodiments, fNIRS can measure the oxygenation status and hemodynamics, which can correspond to brain activity. In such embodiments, a decoded signal can be transmitted to an audio unit 716, a visual unit 602, a transcranial direct stimulation unit (TDCS), or any other know and/or convenient component of another user's interface device 102. In embodiments having a TDCS unit, TDCS can apply an electrical signal to a specific region of another user's brain to communicate brain activity signals. A processor 114 can also save data from original sensor 106 signals and/or decoded signals for documentation or any other known and/or convenient purpose.

In some embodiments, sensors 106 can detect auditory signals from a user and/or the surrounding environment. In such embodiments, sensors 106 can be microphones or any other known and/or convenient device. Signals from these sensors can be sent to a remote processor 114 and/or an onboard processor 714 to be decoded into a signal that can be sent to another user. In such embodiments, a decoded signal can be transmitted to an audio unit 716, a visual unit 602, a haptic unit 718, or any other known and/or convenient component of another user's interface device 102. A storage device 410 can also save data from original sensor 106 signals and/or decoded signals for documentation or any other known and/or convenient purpose.

In some embodiments, sensors 106 can detect visual signals. In such embodiments, sensors 106 can be video-input devices or any other known and/or convenient device. Signals from these sensors can be sent to a remote processor 114 and/or an onboard processor 714 to be decoded into a signal that can be sent to another user. In such embodiments, a decoded signal can be transmitted to an audio unit 716, a visual unit 602, a haptic unit 718, or any other know and/or convenient component of another user's interface device 102. A storage device 410 can also save data from original sensor 106 signals and/or decoded signals for documentation or any other known and/or convenient purpose.

In some embodiments, sensors 106 can detect environmental conditions. In such embodiments, sensors 106 can be temperature sensors, humidity sensors, or any other known and/or convenient device. Signals from these sensors can be sent to a remote processor 114 to be decoded into a signal that can be sent to another user or an onboard processor 714 to provide feedback to a user, such as activation of an environmental control unit 710. In such embodiments, a decoded signal can be transmitted to an environmental control unit 710 or any other known and/or convenient component of another user's interface device 102 to make adjustments to enhance the comfort of a user. A storage device 410 can also save data from original sensor 106 signals and/or decoded signals for documentation or any other known and/or convenient purpose.

In some embodiments, sensors 106 can indicate the position and contact of a user interface device 102 with a user's face. In such embodiments, sensors 106 can be pressure or force sensors (such as, but not limited to piezoelectric sensors), or any other known and/or convenient device. Signals from these sensors can be sent to a remote processor 114 to be decoded into a signal that can be sent to another user or an onboard processor 714 to provide feedback to a user. In such embodiments, a decoded signal can be transmitted to adjustment mechanisms 104 or any other know and/or convenient component of another user's interface device 102 to make adjustments to enhance the comfort of a user. A storage device 410 can also save data from original sensor 106 signals and/or decoded signals for documentation or any other known and/or convenient purpose.

Figure 15B:
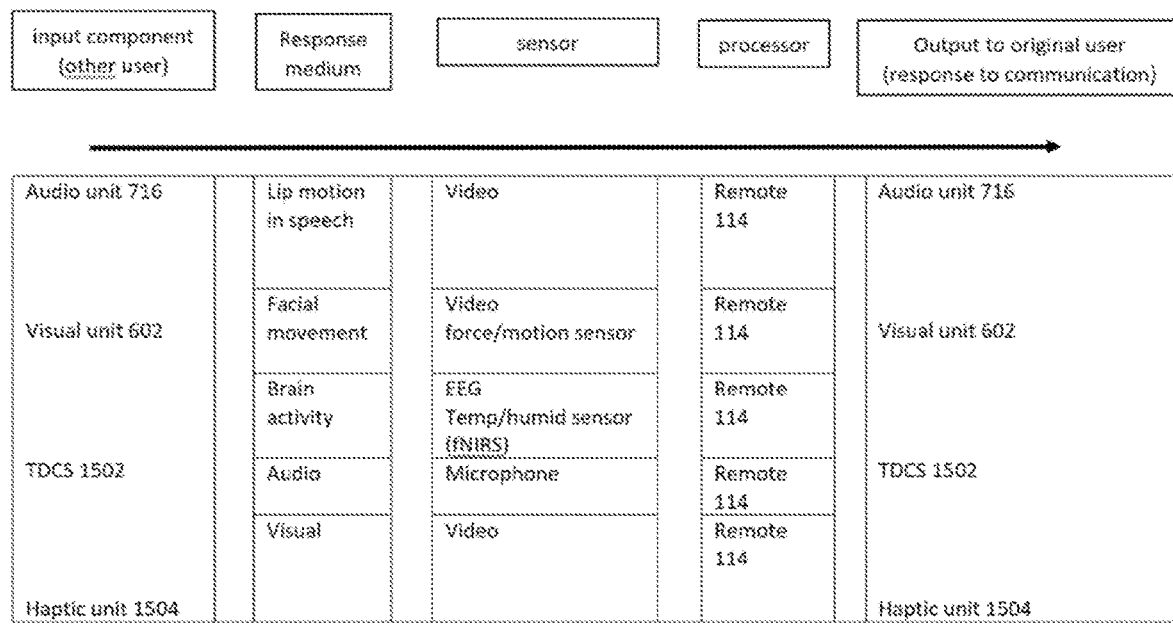
FIG. 15*b* depicts a functional overview of an embodiment of the present system and method.

FIG. 15b depicts a schematic chart of the return path for the overall sensing, communication, and other functions in the present system and method for advanced communication 100. After a remote processor 114 collects data and/or sends a signal to another user in a communicative function, such as, but not limited to, audio, visual, or haptic, a user interface device 102 of another user can construct a response. In such embodiments, another user can send a response in the manner that the original communication was sent.

Figure 16:
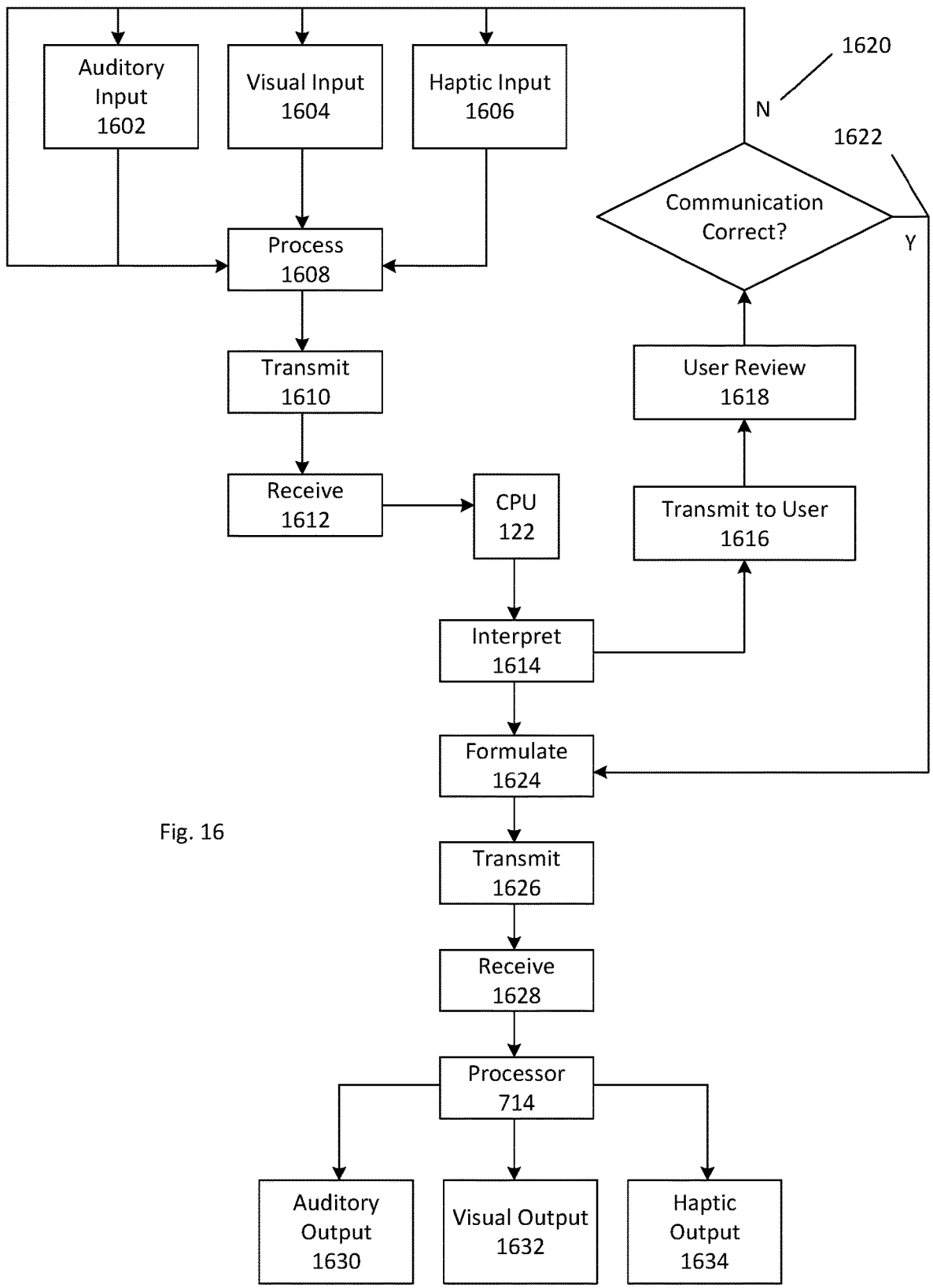
FIG. 16 depicts a flowchart of an embodiment of the present system and method.

FIG. 16 depicts a flowchart of an embodiment of the current system and method. As shown in FIG. 16, a user can provide audio input 1602, visual input 1604, and haptic input 1606 or any other known and or convenient input, via sensors, which can transmit signals 1608 to an onboard processor 714. An onboard processor 714 can transmit signals 1610 to a customized computer hardware system 122 in a remote processor 114, which can receive 1612 interpret said signals into a communication 1614. A customized computer hardware system 122 can transmit the interpreted communication 1616 back to a user for review 1618. If a communication is incorrect, a user can provide input again to correct the communication 1620. If a communication is correct 1622, as verified by a user, a customized computer hardware system 122 can formulate 1624 and transmit a signal 1626, which can be received 1628 by another user's onboard processor 714 and sent to audio output 1630, visual output 1632, and/or haptic output 1634, or any other known and/or convenient output.

Figure 17:
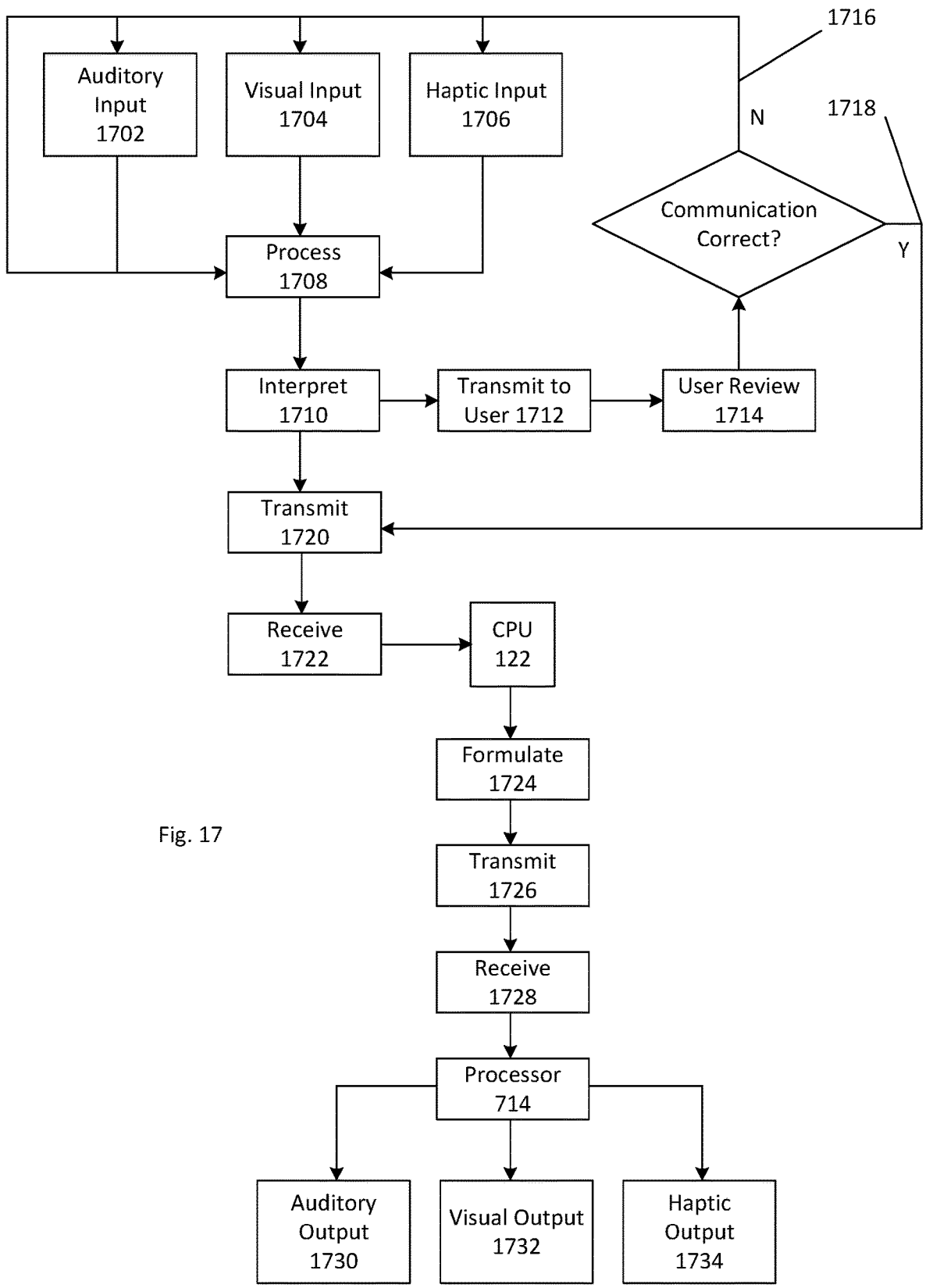
FIG. 17 depicts a flowchart of an alternative embodiment of the present system and method.

FIG. 17 depicts a flowchart of another embodiment of the present system and method. As shown in FIG. 17, a user can provide audio input 1702, visual input 1704, and haptic input 1706 or any other known and/or convenient input, via sensors 106, which can transmit signals 1708 to an onboard processor 714. An onboard processor 714 can interpret said signals 1710 into a communication. An onboard processor 714 can transmit the interpreted communication 1712 back to a user for review 1714. If a communication is incorrect, a user can provide input again to correct the communication 1716. If a communication is correct 1718, as verified by a user, a processor 714 can transmit a signal 1720, which can be received 1722 by a customized computer hardware system 122. A customized computer hardware system 122 can formulate 1724 and transmit a signal 1726 to another user's onboard processor 714, which can receive 1728 and send signals to audio output 1730, visual output 1732, and/or haptic output 1734, or any other known and/or convenient output.

Although exemplary embodiments of the invention have been described in detail and in language specific to structural features and/or methodological acts above, it is to be understood that those skilled in the art will readily appreciate that many additional modifications are possible in the exemplary embodiments without materially departing from the novel teachings and advantages of the invention. Moreover, it is to be understood that the subject matter defined in the appended claims is not necessarily limited to the specific features or acts described above. Accordingly, these and all such modifications are intended to be included within the scope of this invention construed in breadth and scope in accordance with the appended claims.

What is claimed is:

1. An advanced communication system comprising:
   a user interface device, further comprising,
      a base component;
      a plurality of sensors adapted and configured to detect and transmit auditory, visual, and haptic input;
      a plurality of output interfaces adapted and configured to deliver auditory, visual, and haptic output conveying communications;
      a plurality of electromechanical adjustment mechanisms; and
      a lip-reading unit;
   a remote data processing system, adapted and configured to receive and convey audible and non-verbal communications and sensor signals, said system comprising a processor adapted and configured to interpret and evaluate said audible and non-verbal communications and sensor signals;
   a network further comprising,
      a cloud component; and
      at least one communications node.

2. The system of claim 1, wherein said user interface device further comprises a visual unit.

3. The system of claim 1, wherein said user interface device further comprises an oral containment unit.

4. The system of claim 1 further comprising a feedback loop, wherein said remote processing system sends a signal of a decoded communication back to a user for verification before transmitting said communication over said cloud component.

5. The system of claim 1, wherein said user interface further comprises,
   a frame and attachment unit removably connected with a wearable item;
   an environmental control unit and actuating mechanism;
   an energy harvesting unit,
   a communication unit;
   an onboard data processing unit; and
   an audio unit.

6. The system of claim 5 further comprising a feedback loop, wherein said onboard data processing unit sends a signal of a decoded communication back to a user for verification before transmitting said communication to said remote processing system and said cloud component.

7. The advanced communication system of claim 1,
   wherein said sensor in a user interface device is an EEG sensor;
   wherein said EEG sensor is adapted and configured to obtain an EEG measure; and
   wherein said EEG measure is used by said remote processing system in at least one of interpreting and evaluating said audible and non-verbal communications and sensor signals.

8. The advanced communication system of claim 1,
   wherein said sensor in a user interface device is an fNIRS sensor;
   wherein said fNIRS sensor is adapted and configured to obtain an fNIRS measure; and
   wherein said fNIRS measure is used by said remote processing system in at least one of interpreting and evaluating said audible and non-verbal communications and sensor signals.

9. A method for advanced communication, comprising the steps of:

a sensor detecting an auditory, visual, or haptic input signal from a user;

transmitting said auditory, visual, or haptic signal to a remote data processing unit;

said remote data processing unit decoding and interpreting said auditory, visual, or haptic signal as a communication;

transmitting said communication as an electromagnetic signal across a network of other users;

communication units receiving said electromagnetic signal and changing said electromagnetic signal to an auditory, visual, or haptic output signal.

10. The method of claim 9, further comprising the steps of:

transmitting said communication back to a said user for verification;

upon verification, transmitting said communication to said data processing unit.

11. The method of claim 10, wherein said remote data processing unit is included in a user interface device.

12. The method of claim 9, wherein said sensor is associated with an oral containment unit.

13. The method of claim 9, wherein at least one of said steps of transmitting said auditory, visual, or haptic signal to a remote data processing unit and transmitting said communication as an electromagnetic signal across a network of other users is accomplished via at least one communication node.

14. The method of claim 9, further comprising:

Receiving EEG measurement from an EEG sensor;

wherein said EEG measurement is used, at least in part, to interpret said said auditory, visual, or haptic signal.

15. The method of claim 9, further comprising:

receiving fNIRS measurement of oxygenation status and hemodynamics from an fNIRS sensor;

wherein said fNIRS measurement is used, at least in part, to interpret said signal.

* * * * *